United States Patent [19]

Szabo et al.

[11] Patent Number: 4,830,998

[45] Date of Patent: May 16, 1989

[54] HYDROCARBON ISOMERIZATION CATALYST, PROCESS FOR ITS PREPARATION, AND USE THEREOF

[75] Inventors: Georges Szabo; Francois-Xavier Cormerais, both of Montivilliers, France

[73] Assignee: Compagnie De Raffinage Et De Distribution Total France, Levallois-Perret, France

[21] Appl. No.: 74,009

[22] Filed: Jul. 16, 1987

[30] Foreign Application Priority Data

Jul. 16, 1986 [FR] France ................................ 86 10345

[51] Int. Cl.⁴ .......................... B01J 29/12; B01J 29/22
[52] U.S. Cl. ........................................ 502/66; 502/74; 502/78; 502/79
[58] Field of Search .................... 502/78, 79, 66, 74; 585/751, 739

[56] References Cited

U.S. PATENT DOCUMENTS

| | | | |
|---|---|---|---|
| 2,971,903 | 2/1961 | Kimberlin, Jr. et al. | 585/739 |
| 3,409,685 | 11/1968 | Donaldson et al. | 502/78 |
| 3,507,931 | 4/1970 | Morris et al. | 502/78 |
| 3,592,760 | 7/1971 | Young | 502/78 |
| 3,660,309 | 5/1972 | Hayes et al. | 502/66 |
| 3,766,286 | 10/1973 | Olah | 585/739 |
| 4,255,288 | 3/1981 | Cull et al. | 502/66 |
| 4,665,272 | 5/1987 | Bakas et al. | 585/739 |

*Primary Examiner*—Carl F. Dees
*Attorney, Agent, or Firm*—A. Thomas S. Safford; Curtis, Morris & Safford

[57] ABSTRACT

Catalysts for the isomerization of hydrocarbons, particularly normal paraffins having from 4 to 7 carbon atoms, as well as a process for the preparation of the catalyst and a process for their use in the isomerization of such hydrocarbons are disclosed.

The catalysts are composed of a zeolite support impregnated with a mixture of zirconium, a refractory metallic oxide and at least one platinum-group metal.

The process for the preparation of the catalysts involves steps of depositing the zirconium, on the zeolite support, mixing (zeolite+Zr) with alumina, and depositing a platinum group metal on the mixture (zeolite+Zr)/alumina, accompanied by intermediate calcining and shaping steps, and followed by drying and final calcining steps. Alternative methods for depositing the zirconium and platinum group metals on the zeolite are disclosed.

18 Claims, No Drawings

HYDROCARBON ISOMERIZATION CATALYST, PROCESS FOR ITS PREPARATION, AND USE THEREOF

The present invention relates to catalysts for the isomerization of hydrocarbons, and particularly of normal paraffins having from 4 to 7 carbon atoms, to a process for the preparation of these catalysts, and to their use in the isomerization of such hydrocarbons.

There are two types of processes for the isomerization of normal paraffins, namely, processes employing relatively high temperatures, that is to say, temperatures above 200° C., which make use of a catalyst containing a metal from group VIII on an acidic silicoaluminate support, and processes operated at lower temperatures and using a Friedel-Crafts type of catalyst comprising aluminum chloride, for example.

In the high-temperature isomerization processes, it is known to employ catalysts with a zeolite support, of which the most active and the most selective are composed of mordenite or faujasite, either alone or in admixture with a binder consisting of a refractory metallic oxide, such as alumina or silica, supporting one or more platinum-group metals.

Hereinafter, the term "platinum-group metal" will designate one of the following metals: Ruthenium, rhodium, palladium, osmium, iridium, and platinum.

Among the bimetallic catalysts on an aluminosilicate or mordenite support which are capable of facilitating the isomerization of n-pentane to isopentane, metal pairs made up of a platinum-group metal and of a metal from the group consisting of tungsten and chromium are preferred. (See U.S. Pat. No. 3,752,862.)

In investigating these zeolite-supported catalysts, the Applicants have observed however, that the presence of zirconium, in addition to platinum and/or palladium, on the mordenite or faujasite in admixture with alumina has the effect not only of increasing the activity and selectivity of these catalysts but also of facilitating the isomerization of the normal paraffins at lower temperatures and pressures and with higher conversion rates.

The present invention thus seeks to provide new zeolite-supported catalysts that have satisfactory catalytic properties (conversion to and yield of isoparaffins) when used for the isomerization of hydrocarbons.

Hereinafter, "conversion rate" will be used to define the relative disappearance of a normal paraffin, and "isoparaffin yield" the weight ratio of isoparaffin to total feedstock treated.

The present invention consequently has as an embodiment a catalyst for the isomerization of normal paraffins to isoparaffin which is characterized in that it comprises:

(a) From 49.9 to 97 weight percent, and preferably from 80 to 97 weight percent, of a zeolite selected from the group consisting of mordenite and faujasite, (b) from 0.1 to 1 weight percent of zirconium in combined form, (c) from 49.9 to 1 weight percent, and preferably from 19.8 to 1 weight percent, of at least one refractory metallic oxide, preferably alumina, and (d) from 0.1 to 1 weight percent of at least one metal selected from the group consisting of platinum and palladium.

The zirconium content of the catalyst in accordance with the invention is at least equal to its platinum and/or palladium content and is preferably between 0.4 and 0.7 percent by weight of the catalyst.

Moreover, the platinum and/or palladium content of the catalyst in accordance with the invention is preferably between 0.2 and 0.4 percent by weight of the catalyst.

Another characteristic of the invention is that the zirconium and the platinum and/or palladium are deposited on different supports. The zirconium is deposited on a zeolite selected from the group consisting of mordenite and faujasite, after a chemical treatment of the zeolite permitting the replacement of a portion of the alkali-metal ions present with hydrogen ions and the extraction of a portion of the alumina present in the zeolite lattice. The palladium and/or platinum is deposited on the zeolite/alumina support after the zirconium has been deposited on the zeolite.

The present invention has as a further embodiment a process for the preparation of these catalysts which is characterized in that it consists in:

(a) Chemically treating the zeolite for replacement of at least a portion of the alkali-metal ions present in this support with hydrogen ions and for extraction of a portion of the alumina from the zeolite lattice, (b) depositing the zirconium in combined form on the zeolite, (c) admixing the alumina with the zeolite support on which said metal has been deposited, (d) calcining followed by shaping, (e) depositing the metal selected from the group consisting of platinum and palladium, and (f) drying and calcining the catalyst.

The shaping of step (d) may involve extrusion or any other forming method with which those skilled in the art are familiar.

The replacement of at least a portion of the alkali-metal ions contained in the zeolite with hydrogen ions in this process of preparation is known to those skilled in the art. To accomplish this replacement, they frequently resort to the technique known as ion exchange in an acidic medium or in a salt solution. Partial dealumination of the zeolite often improves its catalytic properties. It is generally effected, apart from the ion-exchange technique, by steam treatment followed by acid extraction. However, the degree of dealumination should not exceed a certain value, above which the catalyst is likely to sustain a loss of activity.

The deposition of the zirconium may be effected by impregnating the zeolite with a solution containing a salt of that metal, selected from the group mentioned below, and the acid corresponding to that zirconium salt.

The deposition of the metal selected from the group consisting of platinum and palladium may be effected by impregnating the zeolite/alumina mixture with a solution containing a complex ion of that metal and of an ammonium salt in excess.

In a desire to be precise, the preferred solutions for impregnation of the zeolite and/or the alumina with these metals (zirconium, platinum and palladium) will now be described in greater detail, which, however, should not be construed as a limitation of the invention.

In the specific case of zirconium, the zeolite support is impregnated with an aqueous solution comprising a mixture of a zirconium salt and of its corresponding acid, said salt being selected from the group of the halides, oxalates and other salts of zirconium or zirconyl.

In the case of platinum and palladium, these are deposited by impregnation of the zeolite/alumina mixture with a solution containing a complex ion of platinum or palladium selected from the group consisting of the platinum or palladium complexes, and particularly the aminated complexes, such as platinum dichlorotetramine and palladium dichlorotetramine. For uniform impregnation, it is necessary, moreover, to introduce into the solution another cation, preferably the cation of ammonium obtained from one of its salts, selected from the group consisting of the halides, nitrate or other anions. The ammonium cation and the platinum and/or palladium present in the solution will compete in the exchange reaction with the ions present in the zeolite or alumina.

Another embodiment of the invention may consist of the catalysts prepared in accordance with the process of preparation, described above.

Further embodiments of the present invention consist of the use of the catalyst of the invention for the isomerization of normal paraffins. This use may be characterized in that the catalyst is reduced prior to its utilization in a dry hydrogen atmosphere at a pressure of from 1 to 50 bar, and preferably from 20 to 40 bar, and at an elevated temperature of from 200° to 600° C., and preferably from 400° to 550° C.

Still another embodiment of the invention is an isomerization process employing said catalyst. It may be characterized in that the isomerization of normal paraffins to isoparaffins is carried out at a temperature of from 220° to 280° C., and preferably from 240° to 260° C., and a total pressure of from 2 to 40 bar, and preferably from 5 to 30 bar, with a molar ratio of hydrogen to hydrocarbon ($H_2$/HC) of from 0.5 to 4, and preferably from 1 to 2, and at a weight-hourly space velocity (weight of feedstream per hour per unit weight of catalyst), or W.H.S.V., of from 0.5 to 5, and preferably from 1 to 2.

The results obtained by the isomerization of n-pentane by this process are very satisfactory, as will be seen from the examples given below. The process lends itself to the isomerization of normal butane, normal pentane, normal hexane, a mixture of normal pentane and normal hexane, or a mixture of paraffinic hydrocarbons having from 4 to 7 carbons, and, in fact, any paraffinic hydrocarbon with a boiling point of less than 85° C.

The examples which follow are intended to illustrate the invention without limiting it in any way.

EXAMPLE 1

This example describes the preparation of a catalyst A and of a catalyst A' without zirconium, obtained from a mixture of 50 weight percent of mordenite and 50 weight percent of alumina, on which 0.31 weight percent of platinum (catalyst A) and 0.2 weight percent of palladium (catalyst A') have been deposited.

(1) Chemical treatment of mordenite

The mordenite used is Alite 150, marketed in powder form by Societe Chimique de la Grande Paroisse.

200 g of Alite 150 is dropped into 2 liters of 6N hydrochloric acid. The mixture is refluxed for 6½ hr. Then the solution is filtered and the filtrate is washed with water.

Three exchange reactions are carried out by dropping this filtrate into a 1M solution of ammonium nitrate. The volume ratio of liquid to solid (L/S) of this solution is 10.

This mixture is refluxed for 1 hr. for each exchange. The solution containing the mordenite which has been exchanged three times is filtered.

The filtrate recovered, which corresponds to the hydrogenated mordenite, referred to as mordenite $NH_4^+$, is washed with distilled water and then dried at 120° C. for 18 hr.

After calcination at 650° C., a mordenite H is obtained which is characterized by an Si/Al ratio of 8.7 and a sodium oxide ($Na_2O$) content of 170 ppm.

(2) Shaping of mordenite H/alumina mixture 12.25 g of mordenite H in the form of a powder dried at 120° C. and 15.4 g of xerogel are mulled in the presence of 32 $cm^3$ of triple-distilled water.

The xerogel is prepared by a technique with which those skilled in the art are familiar, that is to say, by reacting aluminum trichloride ($AlCl_3$) or aluminum trinitrate ($Al(NO_3)_3$) with ammonium hydroxide ($NH_4OH$). The xerogel ($Al_2O_3 \cdot H_2O$) obtained by this reaction is filtered and then dried. It is free of sodium.

The mordenite H/alumina mixture which has been mulled is extruded through a die with a diameter of 2 mm. The extrudates are dried overnight at 120° C. and then calcined for 2 hr. at 500° C. after heating has been started in a furnace with a cold muffle.

(3) Deposition of platinum or palladium on mordenite H/alumina extrudates

A 1M solution of ammonium nitrate ($NH_4NO_3$) is circulated for 2 hr. over 22.5 g of the extrudates so that the liquid-to-solid volume ratio L/S of the solution to the extrudates is 5. Then a solution which initially contains 14.9 g of ammonium nitrate ($NH_4NO_3$), 0.162 g of platinum dichlorotetramine ($Cl_2Pt(NH_3)_4 \cdot H_2O$) and 300 $cm^3$ of triple-distilled water is circulated over the solid for 24 hr. This treatment permits the cation containing the platinum $[Pt(NH_3)_4]^{2+}$ to again enter into competition with the ammonium ion $NH_4^+$ in the exchange reaction with the ions of the modenite-$NH_4^+$.

The catalyst A so obtained is dried overnight at 120° C. and calcined for 3 hr. at 500° C.

This catalyst contains only 0.07 percent chlorine.

Catalyst A' is obtained similarly by using 0.13 g of palladium dichlorotetramine ($Cl_2Pd(NH_3)_4$) in place of $[Cl_2Pt(NH_3)_4 \cdot H_2O]$.

EXAMPLE 2

This example describes the preparation of a catalyst B in accordance with the invention which consists of a 50:50 mixture of mordenite H and alumina supporting 0.37 percent of zirconium and 0.30 percent of platinum, and the preparation of a catalyst B' with the same support and containing 0.35 percent of zirconium and 0.20 percent of palladium.

The mordenite H was prepared as described in Example 1.

(1) Deposition of zirconium

A solution containing 0.61 g of zirconium tetrachloride ($ZrCl_4$) in 150 $cm^3$ of 1N hydrochloric acid is introduced into a rotary evaporator which already contains 30 g of mordenite H in powder form. The liquid-to-solid volume ratio L/S of the solution to the mordenite H is 5.

This solution is evaporated. The solid obtained is dried overnight at 120° C. and then calcined for 2 hr. at 500° C. after heating has been started in a furnace with a cold muffle.

(2) Shaping of (mordenite+H+Zr) alumina mixture 30 g of the above calcined solid is mulled with 42 g of xerogel in the presence of 55 cm³ of triple-distilled water. The mulled mixture is extruded through a 2-mm die. The extrudates are dried overnight at 120° C. and then calcined for 2 hr. at 500° C. after heating has been started in a furnace with a cold muffle.

(3) Deposition of platinum or palladium

This deposition is effected as described in Example 1, a 1M solution of ammonium nitrate ($NH_4NO_3$) being circulated for 2 hr. over 31 g of extrudates obtained as described above, the liquid-to-solid volume ration L/S of the solution to the extrudates being 5.

Then a solution composed of 20.5 g of ammonium nitrate ($NH_4NO_3$), 0.23 g of $Cl_2Pt(NH_3)_4 \cdot H_2O$ and 410 cm³ of distilled water is circulated over these extrudates for 24 hr. (For the deposition of palladium, 0.18 g of $Cl_2Pd(NH_3)_4$ is used.)

The catalysts in the form of extrudates are recovered by filtration and then dried overnight at 120° C. They are calcined for 3 hr. at 500° C.

The measured chlorine content is 0.04 percent by weight of the catalyst.

EXAMPLE 3

This example describes the use of the four catalysts A, A', B and B' prepared in Examples 1 and 2 in the isomerization of normal-pentane of a purity of about 97.5 percent.

20 g of catalyst A or A' or B or B' is introduced into a 42-cm³ reactor of a small isomerization pilot unit. The catalysts are conditioned in the reactor by placing the reactor under a hydrogen pressure of 30 bar, with the hydrogen flow rate set at 16.8 liters/hr., and increasing the reactor temperature at the rate of 50° C./hr. to 500° C. and then maintaining it at 500° C. for 3 hr.

The reactor temperature is then reduced to 265° C., at which temperature the normal pentane is introduced into the reactor at a weight-hourly space velocity (W.H.S.V.) of 2, with a hydrogen-to-hydrocarbon ratio $H_2/HC$ of 1.25, at a total pressure in the reactor of 30 bar.

The isomerization results obtained under these conditions and the metal content of the catalysts A and B are presented in Table 1 which follows.

TABLE 1

| Catalyst | Metal content | | | Isomerization | |
|---|---|---|---|---|---|
| | % Pd | % Pt | % Zr | n-Pentane conversion, % | Isopentane yield, % |
| A | | 0.31 | | 59.7 | 59.7 |
| A' | 0.2 | | | 59.4 | 59.4 |
| B | | 0.30 | 0.37 | 63.8 | 63.8 |
| B' | 0.2 | | 0.35 | 63.7 | 63.7 |

The presence of zirconium in the catalysts B and B' promotes the conversion of normal pentane to isopentane with zero cracking, and consequently promotes an increase in the yield of the isomerization reaction by comparison with the catalysts A and A', with the same platinum or palladium content.

EXAMPLE 4

This example describes the isomerization of an industrial feedstock with a catalyst C in accordance with the invention.

The catalyst C employed in this process is composed of 85 weight percent of mordenite H and 15 percent of alumina supporting 0.26 weight percent of platinum and 0.63 percent of zirconium, based on the total weight of the catalyst. It was prepared in the same manner as catalyst B, except that the amounts of the substances used are different.

20 g of catalyst C is introduced into the reactor of the small pilot unit with a capacity of 42 cm³ and conditioned as in Example 3 before the industrial feedstock to be isomerized is charged to it.

This feedstock is a straight-run light gasoline with an octane number (RON) of 70.6. The feedstock has the following composition:

| Constituents | Weight Percent |
|---|---|
| n-Butane | 0.18 |
| Isopentane | 24.25 |
| n-Pentane | 45.01 |
| 2,2-Dimethylbutane | 0.42 |
| Cyclopentane | 1.19 |
| 2-Methylpentane | 9.16 |
| 3-Methylpentane | 4.88 |
| n-Hexane | 11.76 |
| Methylcyclopentane | 1.55 |
| 2,4-Dimethylpentane | 0.11 |
| Benzene | 0.75 |
| Cyclohexane | 0.54 |
| 2-Methylhexane | 0.09 |
| 2,3-Dimethylpentane | 0.05 |
| 3-Methylhexane | 0.06 |
| Total | 100.00 |

This feedstock was isomerized under different conditions in accordance with the isomerization process of the invention. These conditions and the results of the isomerization of this industrial feedstock are presented in Table 2.

TABLE 2

| Temperature, °C. | Total pressure, bar | W.H.S.V. | $H_2/HC$ molar ratio | CONVERSION | | YIELD $C_5^+$ wt. % | Octane number (RON) of isomerizate |
|---|---|---|---|---|---|---|---|
| | | | | $nC_5$ | $nC_6$ | | |
| 260 | 32 | 2 | 2 | 38.8 | 55.7 | 99.0 | 81.4 |
| 250 | 30 | 1.5 | 1.5 | 46.7 | 62.48 | 98.9 | 83.3 |
| 240 | 12 | 1.0 | 2 | 45.1 | 62.2 | 99.0 | 82.9 |

In the light of this table, it is apparent that the isomerization process employing a catalyst in accordance with the invention makes it possible to obtain a gasoline with a high octane number of about 83 and with an excellent yield of isoparaffins.

EXAMPLE 5

This example compares the performance of catalyst C, described in Example 4, with that of an industrial catalyst X comprising a mordenite/alumina support and platinum. These two catalysts are used in the isomerization of n-pentane.

The procedure is the same as that described in Example 4 for catalyst C. (20 g of catalyst C in the 42-cm³ pilot unit.) In the case of catalyst X, the small pilot unit is also loaded with 20 g; however, the volume occupied is only 30 cm³. The same weight-hourly space velocity can then be used as in the isomerization process of the invention. (The loading densities of the two catalysts are different.)

TABLE 3

| Temperature, °C. | H₂/HC molar ratio | Pressure, bar | W.H.S.V. | Catalyst C | | Catalyst X | |
| --- | --- | --- | --- | --- | --- | --- | --- |
| | | | | Yield $C_5^+$ wt. % | RON | Yield $C_5^+$ wt. % | RON |
| 250 | 2 | 18 | 1.0 | 97.8 | 82.9 | 99.3 | 80.8 |
| 240 | 2 | 12 | 1.0 | 98.0 | 82.9 | 99.5 | 80.0 |

It is apparent from the above table that catalyst C in accordance with the invention is more active than the commercial catalyst X in that the octane number (RON) of the gasoline obtained under the same conditions with catalyst C is always higher than that of the gasoline obtained with catalyst X.

What is claimed is:

1. A catalyst for the isomerization of normal paraffins to isoparaffins, comprising:
   (a) from 49.9 to 97 weight percent of a zeolite support selected from the group consisting of mordenite and faujasite;
   (b) from 0.1 to 1 weight percent of zirconium in combined form;
   (c) from 49.9 to 1 weight precent of at least one refractory metallic oxide; and
   (d) from 0.1 to 1 weight percent of at least one metal selected from the group consisting of platinum and palladium.

2. The catalyst according to claim 1, further comprised in that its zirconium content is at least equal to its platinum and/or palladium content.

3. The catalyst according to claim 2, further comprised in that its zirconium content is between 0.2 and 0.7 weight percent.

4. The catayst according to claim 1, further comprised in that its content of metal selected from the group consisting of platinum and palladium is between 0.2 and 0.4 weight percent.

5. A catalyst according to claim 1, wherein the zirconium has been deposited on a zeolite having a typical lattice and being selected from the group consisting of mordenite and faujasite, and said deposition having occurred after a chemical treatment of said zeolite to replace a portion of the alkali-metal ions present with hydrogen ions and to extract a portion of the alumina present in the zeolite lattice.

6. A catalyst according to claim 1, wherein said zeolite ranges from 80 to 97 weight percent, and said refractory metallic oxide ranges from 19.8 to 1 weight percent.

7. The catalyst according to claim 1, wherein the metal selected from the group consisting of palladium and platinum is deposited on the zeolite/zirconium-/alumina mixture.

8. A process for the preparation of a catalyst for the isomerization of normal paraffins to isoparaffins comprising the steps of:

chemically treating a zeolite support selected from the group consisting of mordenite and faujasite to replace at least a portion of the alkali-metal ions present in the support with hydrogen ions and to extract a portion of the alumina present in the zeolite lattice;

depositing zirconium on the zeolite;

mixing alumina with the support;

calcining the mixture obtained;

shaping the calcined mixture;

depositing a metal selected from the group consisting of platinum and palladium on the mixture;

drying and calcining the mixture on which the platinum and/or palladium has been deposited.

9. The process according to claim 8 further comrised in that the deposition of the zirconium is effected by impregnation of the zeolite support with a solution containing a zirconium salt selected from the group consisting of the halides, oxalates and all other salts of zirconium and zirconyl, and an acid corresponding to the salt selected.

10. The process according to claim 8 further comprised in that deposition of a metal selected from the group consisting of platinum and palladium is effected by impregnation of the zeolite support with a solution containing a complex ion of a metal, selected from the group consisting of the complexes of platinum and palladium, and an excess of an ammonium salt, selected from the group consisting of the halides, nitrates and all other salts of ammonium.

11. The process according to claim 10 wherein the complexes of platinum and palladium are the aminated complexes.

12. The process according to claim 9 wherein the aminated platinum and palladium complexes are platinum dichlorotetramine and palladium dichlorotetramine, respectively.

13. A catalyst prepared according to the process of claim 8.

14. A catalyst prepared according to the process of claim 12.

15. The process according to claim 8 further comprised in that the catalyst is reduced under a dry hydrogen atmosphere at a pressure of from 1 to 50 bars and at a temperature of from 200° to 600° C.

16. The process according to claim 15 wherein the dry hydrogen atmosphere is at a pressure of from 20 to 40 bars and the temperature is from 400° to 550° C.

17. The process according to claim 8 wherein replacement of the portion of the alkali-metal ions present in the zeolite support with hydrogen ions is performed by ion exchange in an acidic medium or in a salt solution.

18. The process according to claim 8 wherein extraction of a portion of the alumina present in the zeolite is by steam treatment followed by acid extraction.

* * * * *